United States Patent

Abend et al.

[11] Patent Number: 5,870,182
[45] Date of Patent: Feb. 9, 1999

[54] SYSTEM FOR CHECKING A SUSPENSION OF FLUORESCENT MATERIAL

[75] Inventors: Klaus Abend, Essingen; Gert Ferrano, Aalen; Albert Aich, Westhausen, all of Germany

[73] Assignee: TIEDE GmbH & Co. Rissprüfanlagen, Essen, Germany

[21] Appl. No.: 836,678
[22] PCT Filed: Oct. 14, 1995
[86] PCT No.: PCT/DE95/01419
§ 371 Date: Jul. 14, 1997
§ 102(e) Date: Jul. 14, 1997
[87] PCT Pub. No.: WO96/13718
PCT Pub. Date: May 9, 1996

[30] Foreign Application Priority Data

Oct. 30, 1994 [DE] Germany .................. 44 38 510.2

[51] Int. Cl.⁶ .................. G01N 21/64; G01N 21/59
[52] U.S. Cl. .................. 356/73; 250/373; 250/461.1; 356/417
[58] Field of Search .................. 356/73, 317, 318, 356/417; 250/373, 461.1, 458.1; 73/61.65, 61.69, 61.711

[56] References Cited

FOREIGN PATENT DOCUMENTS

| | | | |
|---|---|---|---|
| 2100013 | 7/1972 | Germany | G01N 21/16 |
| 4311543 | 10/1994 | Germany | G01N 21/64 |
| 0427996 | 5/1991 | WIPO | G01N 21/64 |

OTHER PUBLICATIONS

Patent Abstracts of Japan, Publication Number JP57061944 "Control Method of Magnetic Powder Concentration in Wet Type Magnetic Powder Flaw Detection Test" (1 page).
Patent Abstracts of Japan, Publication Number JP62255851, "Method and Instrument For Measuring Coagulating Sedimentation Reaction" (1 page).

Primary Examiner—F. L. Evans
Attorney, Agent, or Firm—Steinberg & Raskin, P.C.

[57] ABSTRACT

The invention relates to a system for checking a suspension of solid particles, having a test tube for taking up and sedimentation of the suspension, having—an illuminating radiation source (L),—a test tube (P) is transparent to the illuminating radiation and the radiation emerging thereof, in which test medium is allowed to sediment and which can be located in the radiation path of the system,—optionally, a further test tube (PE), that is transparent to the illuminating radiation and the radiation emerging thereof, in which a reference or calibration liquid is allowed to sediment and which can be located in the radiation path of the system,—a sensor device to detect the illuminating radiation ($S_L$)—a sensor device for detecting radiation emerging by transmission ($S_T$) from the test tube(s) ($P_E$, P)—a sensor device for detecting the radiation ($S_F$) emerging from the test tube(s) at an angle other than 180°—a timer device (U) and—a computer (R) for processing the measured values obtained and outputting at least one output signal to the processing unit.

25 Claims, 3 Drawing Sheets

SYSTEM FOR CHECKING A SUSPENSION OF FLUORESCENT MATERIAL

FIELD OF THE INVENTION

The invention relates to a system for checking a suspension of solid particles, in a test tube for taking up the suspension and allowing it to sediment therein.

BACKGROUND OF THE INVENTION

Suspensions of solid particles in liquids are frequently used in technical fields—for example, suspensions of barium sulphate in liquid as contrast medium for X-ray examination equipment, magnetizable, fluorescent particles in liquids for crack testing; lubricating oils, which as time goes on acquire an increased solid content of metallic fines, abrasive suspensions, etc.

Many of these suspensions are circulated in systems—for example, as lubricants or even the fluorescent fluid in crack testing equipment. The ability of the test equipment to make a statement depends, amongst other things, on these suspensions being intact—if there are too few solid particles or if they have been damaged by mechanical stress, the test results obtained with them are often poor or no longer usable. The opposite case also exists where, for example, an increased input of solids into a liquid and therefore the formation of an ever increasingly concentrated suspension has to be checked, so that a statement can be made regarding the continued suitability of the medium—for example, a lubricating oil—in order to prevent damage to an engine. On the other hand it is desirable, both from the environmental and cost points of view, to use the suspension for as long as possible, in order to avoid unnecessary disposal.

Actually most engine oils and also most crack detecting agents are changed after a pre-determined "service interval", as a preventive measure—although for many applications this should not be necessary. On the other hand increased stress on the suspension—for example, from the action of particularly high shearing forces on the liquid and also when working at high temperature—the suspension may degrade more quickly or be "used up".

Hitherto such suspensions, in the case of conductive materials, were often tested by way of conductivity tests (for retarding agents), pH value measurements or even by sedimentation and visual observation thereof in a so-called ASTM bulb. The conductivity test had the disadvantage that even a slight change in the electrolyte or water content of oil, for example, led to completely incorrect measurements—the ASTM bulb had the serious drawback of up to now delivering values that were not automatically acquirable and could therefore only be measured subjectively.

From EP-A-O 427 996 discloses a process for measuring aromatic hydrocarbons, where fluorescence spectroscopy is used to measure the concentration of fluorescent, i.e. liquid-dissolved hydrocarbons. In other words, in this case, clear liquids and not suspensions are being measured.

DE-A-43 11 543 relates to a device for determining the concentration of a test liquid, which only measures the luminescence, i.e. the light emitted by the test liquid but not whether this lunescence may possibly change in time and therefore does not permit any statement to be made as to whether the luminescence occurs as a result of abraded fluorescent material or as a result of the particles themselves, to which the fluorescrible material is bound. This document also does not enable any measurements to be made of the solid density of the suspension, since the emission of fluorescent light does not enable any such statements to be made.

JP-A-62-255851 in turn, relates to the measurement of the rate of sedimentation of a material, as required for coagulation measuring devices, for example for the solvent coagulation of plastics. In other words, the increase in size of the suspended particles is measured over time. The area of the invention on the other hand, relates to the measurement of fluorescent material, which over a period of time, also decreases in size.

OBJECTS AND SUMMARY OF THE INVENTION

Consequently, it is the object of the invention to provide a system which automatically, reliably and verifiably checks the functional performance of suspension of solids in liquid.

The problem is solved according to the invention by a system for checking a suspension of solid particles, in a test tube for taking up the the suspension and allowing same to sediment therein with: an illuminating radiation source (L), a test tube (P) that is transparent to the illuminating radiation and the radiation emerging from the same, and which can be located in the radiation path, optionally, a further test tube (PE) that is transparent to the illuminating radiation and the radiation emerging from the same, in which a reference or calibration liquid is allowed to sediment and which can be located in the radiation path, a sensor device to detect the illuminating radiation (SL), a sensor device for detecting radiation emerging by transmission (ST) from the test tube (s) (PE, P), a sensor device for detecting the radiation (SF) emerging from the test tube(s) at an angle other than 180°, a timer device (U) to initiate the recording of measured values, taken at intervals, thereof solid suspension introduced into the test tube and for introducing new solid suspensions after pre-determined time intervals; and a computer (R) for processing the measured values obtained and outputting at least one output signal to the processing unit. Any known illuminating devices, such as LASER or even UV lamps, normal lamps etc. may be used for this. For test tubes, round but also square, cuvette-type containers, which allow problem-free transmission and also satisfactory cleaning, can be considered.

Preferably the system is checking a suspension of fluorescent or phosphorescent material, having a source of excitation radiation with radiation within the fluorescence/phospho-rescence excitation wavelength range, a test tube (P) that is transparent to the illumination radiation and to the fluorescence and/or phosphorescence radiation emerging thereof, in which test medium is allowed to sediment and which can be located in the radiation path of the system; optio-nally, a further test tube (PE) that is transparent to the illumination radiation and the fluorescence/phosphorescence radiation emerging thereof, in which a reference or calibration liquid is allowed to sediment and which can be located in the radiation path of the system; a sensor device for detecting the illumination radiation (SL); a sensor device for detecting the radiation emerging from the test tube(s) (PE, P) by transmission (ST); a sensor device for detecting fluorescence and/or phosphorescence radiation (SF) emerging from the test tube(s); a timer device (U) which enables measured values to be taken and duly stored after pre-determined intervals; and also a computer (R) for processing the measured values obtained and outputting at least one output signal to the processing unit.

The system according to the invention is preferably arranged in such a way that the test tube (P) is connected to the bypass of a system that is continuously circulating suspension, i.e. constant—and automatable—monitoring of the test medium and documentation of the monitoring values to satisfy documentation obligations are possible.

Preferably the fluorescent solid material of the test medium suspension has particles combined with fluorescent or phosporescible dye.

It may be beneficial if the wavelength of the illumination source has only a small band width, for example, by connecting a band filter in series or by using a laser—this eliminates interference from other wave ranges more reliably.

Particularly suitable as sensor devices for measuring fluorescence/phosphorescence (SF) are sensors protected by cut-off or band filters, which eliminate wavelengths at least in the area of the excitation wavelengths.

Usually the computer (R) processes the measured values of the transmission radiation and the radiation emerging from the test tube at an angle other than 180°, after predetermined time intervals, compares the values thus obtained with a stored rating table and produces at least one corresponding output signal.

This minimum of one output signal from the computer (R) is output to a display unit (D), such as an acoustic sensor, a monitor, a pointer instrument etc.

Preferably at least one output signal from the computer (R) is used to control the renewal of a suspension, to supplement a suspension or to shut down the system working with the suspension.

At least one output signal will be preferably transmitted to a recording unit to generate permanent records on storage media, such as print-outs, test documents or CD-ROM etc., which produce test documents about the quality of the fluorescent suspension under the recording conditions.

Preferably a recording device to make a permanent record of the signal(s) produced, such as a printer etc., shall be connected downstream of the indicating display device (20) or any corresponding visual display unit.

Because now for the first time a system is being proposed that is automatable and even capable of operating continuously and which transmits information at regular intervals concerning the operational capability of the suspension, it is possible, for the first time, to document the function of the suspension, for example, in the form of test documents and, as a result, to meet claims for compensation or even to satisfy requirements imposed by ISO 9000.

Although the system is explained below with the help of fluorescent crack detecting agents, it is taken for granted by the expert in the field of optical testing methods, that the system can also be used, mutatis mutandis, to check other suspensions, where a corresponding evaluation program is then used. What is particularly important is the evaluation in time of the data, as this reflects the sedimentation behaviour and the change with time.

BRIEF DESCRIPTION OF THE DRAWINGS

The invention is described in more detail below with the help of an embodiment, namely a system for checking a fluorescent crack detecting agent and the accompanying drawing, but is in no way limited to this.

DETAILED DESCRIPTION OF THE INVENTION

Figure 1:
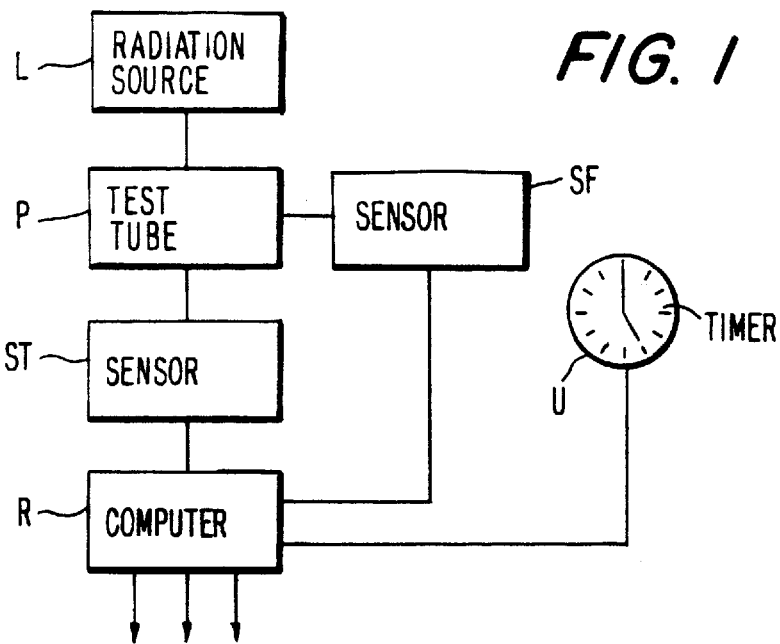
FIG. 1 shows a block diagram of an initial embodiment of a system according to the invention.
Figure 3:
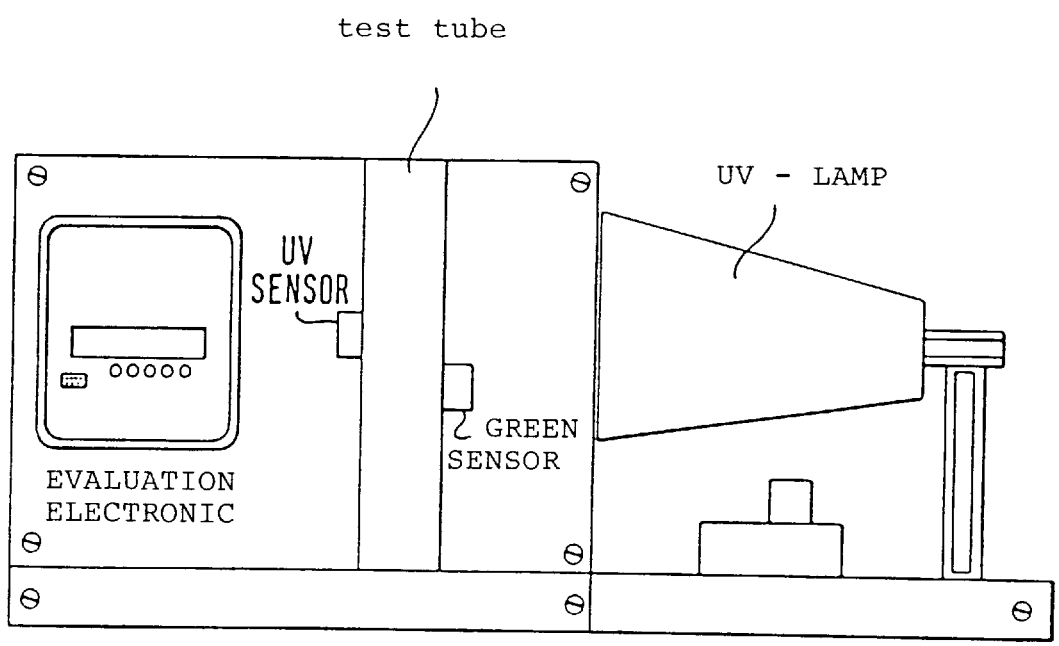
FIG. 3 shows a schematic representation of an automatable test medium measuring unit.

As shown in FIG. 1 and FIG. 3, these are systems that are used as additional equipment in a cost-control package and/or safety documentation as an addition to a crack detection system, in particular one that operates automatically, where the test tube P is transilluminated by a lamp L, acting as the source of radiation and the radiation passing through the test tube by transmission (ST) is measured, preferably at 180° to the direction of irradiation. A further sensor SF is provided for radiation that does not emerge in the direction of transmission, where this sensor SF measures either only certain wavelengths of the emerging light (by the connection of band filters upstream) or the total radiation, using measures that are actually known.

Both values measured by the sensors are transmitted together with a timer value (U) to the computer R, which then processes them into at least one output signal, which can then be transmitted to printers or display instruments and used as a control signal for remote systems etc.

Figure 2:
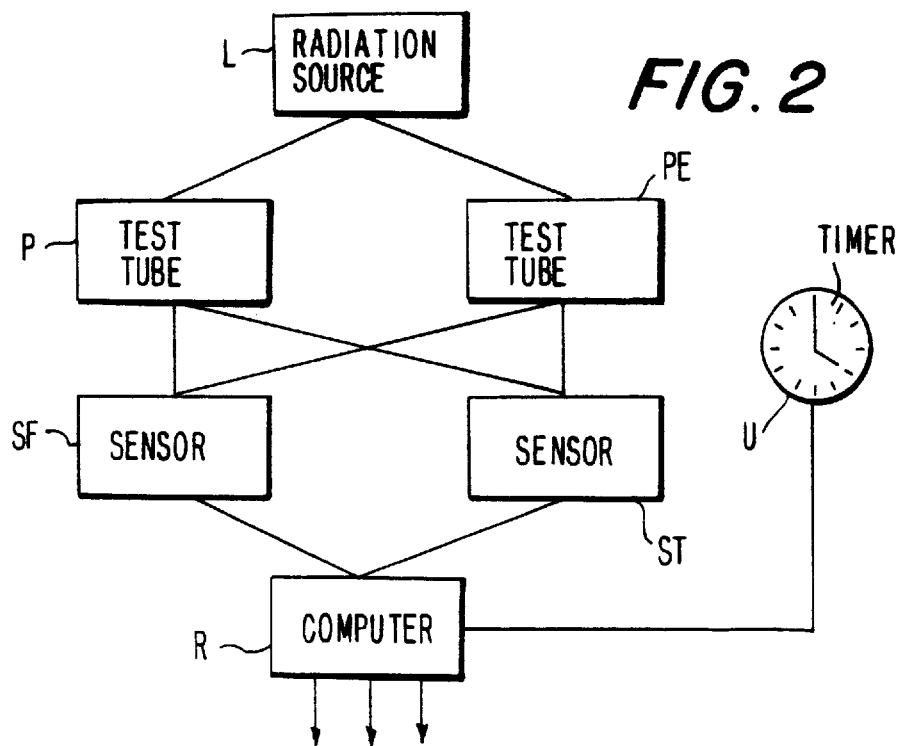
FIG. 2 shows a block diagram of a further embodiment of a system according to the invention.

FIG. 2 shows a more elaborate system, which makes it possible simultaneously to check a test medium in a calibration test tube. Known calibration liquid—for example unused test medium—or even a white standard etc., can be introduced into this calibration test tube, thus providing a permanent measurement reference. The radiation source can be used, by known means (beam divider etc.), to illuminate both test tubes evenly—the same applies to the sensors.

In the embodiment in FIG. 2 the measurement is even more accurate because of the internal standard.

In systems where the devices according to the invention are preferably used, workpieces are magnetized for the magnetic particle test by a known method, they are sprayed with a test medium containing dyes, in particular also ferromagnetic material having fluorescent dyes, such as test media containing iron or an iron compound, with concentration of iron particles on surface flaws and said workpieces are observed under UV or visible light and the crack image thus obtained is compared with the crack image on at least one check test body.

This provides regular checking of the circulating fluid marking medium—which after dripping off the test specimen is regularly recovered in a collecting tank and re-used—for function, ageing, loss of magnetizable particles—because residual particles are usually left behind on the test specimens. The life of the medium and the accuracy of the technique for which it is used can now be drastically improved. It is also recommended that the irradiation devices be regularly checked for their operational capability—it was discovered that the UV lamps, which were mostly used to generate fluorescence, have to be checked both in respect of their spectrum, on account of lamp ageing etc., and also on account of deterioration in function of the lamp as a result of soiling, which can result in a distorted image—irrespective of the functions of cost control and/or warranty. Because the function of the checking system and of its individual components can now also be carried out automatically at pre-set intervals, the following advantages are provided:

the test medium suspension only has to be replaced or a resupply organised once it is known that it is exhausted and no longer delivers satisfactory test results.

The lamps must be constantly checked for their emission. This means that any drop in UV intensity within the lamp spectrum, as is generally known, can be compensated for by appropriate measures—either the lamp can be replaced, its operating voltage adjusted or even the sensitivity of the sensors correspondingly re-calibrated, to compensate for the reduced fluorescence brought about by reduced radiation intensity and to recalibrate the statement of fluorescence intensity in relation to the specific equipment.

Because an automated test medium device, referred to as an "automated ASTM bulb", is provided, it can be ensured that changes in the test medium suspension, which consists of a liquid containing ferromagnetic particles suspended in it, preferably stained with a fluorescent dye, as can be detected by abrasion or disintegration of the ferromagnetic particles where the liquid is circulated for a long period, by dye being deposited on the particles or even loss of magnetic particles, which remain on the various test bodies measured, are detected and the appropriate action taken. Thus, either a new suspension can then be used, ferromagnetic particles be added to the suspension or at least new suspension re-ordered.

The test medium, e.g. the fluorescent, yellowish-green concentrate of the applicant, which contains additives, is subject to a check after pre-determined check intervals, for example, roughly every two hours after the start of processing, using a known bulb-shaped control container (known as an "ASTM bulb"), which is provided with a level mark and in which, following a settling time of 60 minutes, the level of the precipitation is measured according to the graduation lines, thereby determining whether the test liquid can still be used or not or whether fresh indicator (particles) have to be added to the fluid. The relevant values are known to the expert in the field (see in particular, FIG. 4). In other words, it is important in the case of a test system which runs continuously for days or similar periods or which even operates intermittently to generate at least one signal quickly and reliably, providing a continous and constantly available check and which indicates whether the work can be continued with the current test agent or how much longer it will still be available for use or whether a new test agent should be supplied. Processing the test signals obtained from the measuring devices, can lead to considerable savings in test media.

To measure the cost of the test medium material parameter, the test medium is checked by measuring the optical density and the fluorescent behaviour—preferably automatically, at regular intervals.

Figure 4:
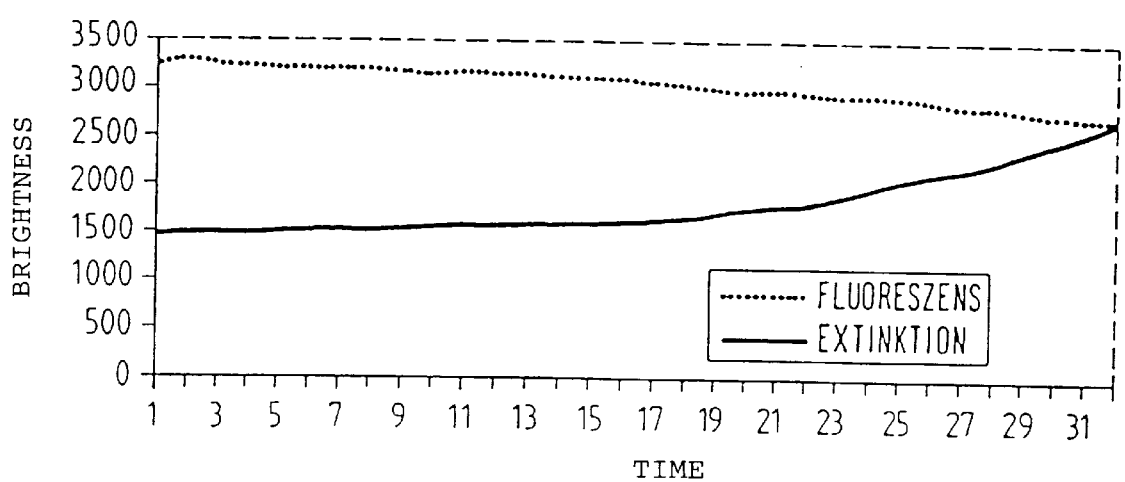
FIG. 4 shows the dependence of fluorescence and transmission of the test medium, as measured by the unit shown in FIG. 4, upon time.

For this purpose, as can be seen from FIG. 4, a test medium suspension, consisting of a liquid carrier and ferromagnetic, fluorescent particles is tapped from the test medium circuit of the test system, is introduced into a test tube or cuvette and left to stand so as to leave a liquid that is still and non-turbulent, suitable for testing. The density of this still liquid is then measured in transmission using the known sensor and the fluorescence is simultaneously measured by a sensor set to the wave length of the fluorescence radiation (in this case in the green area, as the fluorescence occurs there). From the time of introducing test medium into the test tube, measured values are taken at various time intervals. In each case, an initial value for transmission and fluorescence is measured after introducing the fluid test medium suspension into the test tube and at least one further value is measured in each case for T and F at time T after introduction.

As the test medium ages, so too does the size of the particles and their fluorescibility. This leads to measured values which are depicted schematically in FIG. 5. Thereafter, there is an increase in extinction because of the increasing proportion of smaller, slowly sinking particles caused by abrasion and the fluorescence decreases because the fluorescent material, as a result of radiation, is subject to photochemical and general ageing because of the mechanical stress on the same, as well as to further stress.

Hence, the testing medium test unit can measure the following variables with accuracy and these result in an output signal from the test medium test unit, indicating the suitability of the test medium—the ingress of dirt in the test medium, for example, abrasion from workpieces etc., manifests itself as falling transmission and decreasing fluorescence at the start of measurement (To); the penetration of water is shown in the form of rising transmission at (To) and the removal of water is shown as increased concentration of particles, i.e. falling transmission and increasing fluorescence. Where particles are lost, the initial fluorescence (Fo) decreases and where fluorescent material is abraded, fluorescence is maintained in the remaining liquid, once the magnetic particles, which are heavier than water, have sedimentd—in other words the liquid of used test medium fluoresces more intensely after settling, than when the test medium is working properly (FT).

It is preferred that the test tube is developed as a kind of self-cleaning flow cuvette—in other words, on completion of the measurement, new liquid flows through the test tube, thus cleaning it. A separate CIP unit (cleaning-in process) for test tubes, may also be provided to release impurities which cannot be removed by the test medium, such as burnt or polymerised organic compounds, which may clog the test tube and thus lead to the distortion of measurements. Instead of an indicator display unit or digital visual display unit (such as a counter or similar to display the output signals from the computer), these measurements can be transmitted to a print unit, e.g. a laser printer or an ink-jet printer. The values that have been measured or are to be monitored are printed out as documents on a relevant recording material, such as writing paper, during the course of operation over several days, as well as over longer or even shorter operating periods. An appropriate timer (U) thus produces, for each time unit, a control document which in particular, allows subsequent checking of workpiece components or similar. In this case it is possible to correlate the individual statistical values of the workpiece flow, such as type or number of part, number of units or other designation with the data from one or more measured value units.

The test document also serves as information about a pre-set error variable interval as a function of time and about the type of workpiece.

The safety and control document also permits more reliable subsequent control of operators working on VDUs, so that, for example, assessments of the marking element 20$d$ in the colour fields, can be checked and optionally, corrected.

Measurement of the data flow that goes back to brightness values can also be beneficially carried out by a diode cell or other suitable means, as are known to the expert, instead of a camera. The documentation can, of course, be generated remotely and stored by the device, by remote data transfer.

Although the invention has been explained on the basis of a preferred embodiment, the expert is familiar with modifications which fall under the scope of protection of the claims. The invention is therefore, in no way limited to the form of embodiment described.

We claim:

1. A system for checking a suspension of particles, comprising
   an illuminating radiation source for emitting an illuminating radiation;
   a test tube for receiving a suspension of particles, the test tube being situated in a radiation path of the illuminating radiation source, the test tube being transparent to the illuminating radiation from the radiation source, the test tube being transparent to radiation emerging from the test tube;
   a first sensor for measuring radiation emerging from the test tube at a 180 degree angle relative to the radiation path;
   a second sensor for measuring radiation emerging from the test tube at a non-180 degree angle relative to the radiation path;
   a timer for initiating a recording of the measured values from the first and second sensors at intervals; and
   a computer for processing the measured values obtained and outputting at least one output signal.

2. The system according to claim 1, wherein the illuminating radiation source emits radiation in the fluorescence/phosphorescence excitation wavelength range of the particles.

3. The system according to claim 1, further comprising
   a further test tube, the further test tube being situated in a second radiation path of the illuminating radiation source, the further test tube being transparent to the illuminating radiation from the radiation source, the further test tube being transparent to radiation emerging from the further test tube; and wherein
      the first sensor is for measuring radiation emerging from the test tube and the further test tube at a 180 degree angle relative to the respective radiation paths; and
      the second sensor is for measuring radiation emerging from the test tube and the further test tube at a non-180 degree angle relative to the respective radiation paths of the illuminating radiation source.

4. The system according to claim 3, wherein the test tube contains a suspension of particles to be evaluated, and wherein the further test tube contains a reference liquid.

5. The system according to claim 4, wherein the computer compares the radiation emitted from the test tube measured by at least one of the first and second sensors with the radiation emitted from the further test tube measured by at least one of the first and second sensors.

6. The system according to claim 2, further comprising a band filter disposed between the test tube and the second sensor, the band filter excluding a band of wavelengths, the band of wavelengths including the excitation wavelengths.

7. The system according to claim 1, further comprising
   a processing device including, a mechanism for circulating the suspension of solid particles through the processing device; and wherein
      the test tube being selectively coupled to the mechanism to receive the suspension of particles.

8. The system according to claim 7, wherein, the computer is coupled to the processing device, the computer controlling the processing device to perform one or more of a suspension renewal, a suspension supplementation, and a system shut down.

9. The system according to claim 1, wherein the computer processes the measured values received from the first and second sensors, compares the measured values with a stored rating table, and outputs a signal indicative of a result of the comparison.

10. The system according to claim 9, wherein the measured values from the first and second sensors processed by the computer include values measured by the first and second sensors just after introduction of the suspension into the test tube, and values measured by the first and second sensors at a time T after introduction of the suspension into the test tube.

11. A system for checking a suspension of particles, comprising
    an illuminating radiation source for emitting illuminating radiation;
    a first sensor for measuring radiation,
    test tube for receiving a suspension of particles arranged in a radiation path of the radiation source between the radiation source and the first sensor such that the first sensor measures radiation emerging from the test tube at a 180 degree angle relative to the radiation path, the test tube being transparent to the illuminating radiation from the radiation source and to radiation emerging from the test tube;
    a second sensor for measuring radiation emerging from the test tube at a non-180 degree angle relative to the radiation path;
    a timer for initiating timed recording of the measured radiation from the first and second sensors; and
    a computer coupled to the timer for processing the measured radiation obtained from the first and second sensors and outputting at least one output signal.

12. The system according to claim 11, wherein the radiation source emits radiation in the fluorescence/phosphorescence excitation wavelength range of the particles.

13. The system according to claim 11, further comprising
    an additional test tube arranged in a second radiation path of the radiation source between the radiation source and the second sensor, the additional test tube being transparent to the illuminating radiation from the radiation source and to radiation emerging from the additional test tube;
    the first sensor being arranged to measure radiation emerging from the test tube and the additional test tube at a 180 degree angle relative to the respective radiation paths;
    the second sensor being arranged to measure radiation emerging from the test tube and the additional test tube at a non-180 degree angle relative to the respective radiation paths.

14. The system according to claim 13, wherein the test tube contains a suspension of particles to be evaluated, and wherein the additional test tube contains a reference liquid.

15. The system according to claim 14, wherein the computer compares the radiation emitted from the test tube measured by at least one of the first and second sensors with the radiation emitted from the additional test tube measured by at least one of the first and second sensors.

16. The system according to claim 14, wherein the reference liquid includes a fluorescent solid material comprising fluorescent or phosphorescent dye.

17. The system according to claim 12, further comprising a band filter disposed between the test tube and the second sensor, the band filter excluding a band of wavelengths including the excitation wavelengths.

18. The system according to claim 11, further comprising
    a processing device including a mechanism for continuously circulating the suspension of particles through the processing device, the test tube being selectively coupled to the mechanism to receive the suspension of particles.

19. The system according to claim 18, wherein, the computer is coupled to the processing device, the computer controlling the processing device to perform one or more of a suspension renewal, a suspension supplementation, and a system shut down.

20. The system according to claim 11, wherein the computer processes the measured radiation received from the first and second sensors, compares the measured radiation with a stored rating table, and outputs a signal indicative of a result of the comparison.

21. The system according to claim 20, wherein the measured radiation from the first and second sensors processed by the computer include values measured by the first and second sensors just after introduction of the suspension into the test tube, and values measured by the first and second sensors at a time T after introduction of the suspension into the test tube.

22. The system according to claim 11, wherein the radiation source has a small band width.

23. The system according to claim 11, wherein the at least one output signal is transmitted to a recording unit to generate permanent records on storage media to enable the production of test documents about the suspension of particles being checked.

24. The system according to claim 11, wherein the at least one output signal is output to a display unit.

25. The system according to claim 24, wherein the at least one output signal is directed to a recording device connected to the display unit.

* * * * *